July 4, 1961 A. M. SHAMMARELLO Plant Pat. 2,069
ILEX PLANT
Filed March 17, 1960
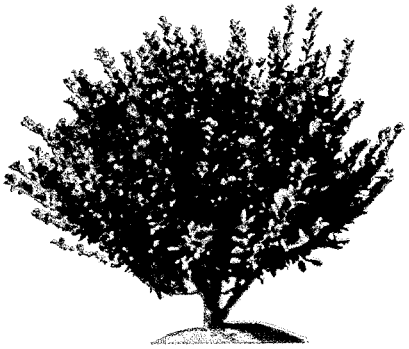
INVENTOR.
A. M. Shammarello
BY Robb & Robb
Attorneys United States Patent Office Plant Pat. 2,069
Patented July 4, 1961

2,069
ILEX PLANT
Anthony M. Shammarello, 4590 Monticello Blvd., South Euclid, Ohio
Filed Mar. 17, 1960, Ser. No. 15,776
1 Claim. (Cl. 47—59)

My present invention comprises a new and distinct variety of ilex plant, my new variety being a seedling of the unpatented variety *Ilex crenata convexa.*

The development of my present new variety has resulted from a program which I have been conducting of careful selection and cross-breeding with the view of producing new varieties of ilex plants of more dwarf and compact form having improved growth characteristics, including greater density of branches and less requirement for trimming so as to make such plants more desirable for hedges and like plantings.

The objectives of the foregoing development program have been attained to a high degree in reference to my present new and distinct variety of ilex plant, characterized by its dwarf, compact, rotundate, and uniform habit of growth slightly taller than its width and with branches dense and elliptical.

My new variety is a dwarf, compact plant, slightly taller than its width. The form of the plant is rotundate, though low branched. The branches of my new variety are dense and elliptical, the growth being more dense than that of its parent. The growth of my new variety is quite uniform thus requiring a minimum amount of trimming.

My new variety is distinctive in its character of growth and foliage being comparable in these respects to a boxwood.

My new variety is extremely hardy and less susceptible to mite than its parent.

My new variety has been found to retain its distinctive characteristics through successive asexual reproduction. Such asexual reproduction has been accomplished by means of cuttings in the vicinity of South Euclid, Ohio.

The accompanying drawing forming a part hereof shows a typical plant of my new variety of ilex.

The following is a detailed description of my new variety of ilex plant:

Color references are to Nickerson Color Fan as published by Munsell Color Company.

Parentage: Seedling of *Ilex crenata convexa.*

Habit of growth: Plant is a dwarf compact grower. The habit of growth is rotundate, low branched; branches are dense and elliptical.

Young shoots: Stems—color—moderate reddish brown 2.5YR 3/3.

Mature shoots: Stems—color—moderate olive 5Y 4/3.

Foliage: Arrangement is alternate. The individual leaves are smaller in shape and slightly convex, whereas the parents' are larger and convex. Form—18 mm. long (ranging 10 mm. to 20 mm. long) and 10 mm. wide, oval at tips of leaves; slightly serrated, narrower at base into petiole; petiole is 3 mm.

Color of young leaves: Face—moderate yellow green 5GY 5/6. Back—moderate yellow green 2.5GY 5/5.

Color of mature leaves: Face—moderate olive green 7.5GY 4/4. Back—moderate yellow green 5GY 5/6. By way of comparison the color of the foliage is a lighter green than its parent.

Flowers: Pistillate.
- *Borne.*—Singular.
- *Size.*—5–6 mm.
- *Color.*—Greenish white 7.5BG 9/1.
- *Pedicels.*—5–6 mm.

Fruit:
- *Form.*—Round.
- *Size.*—4–5 mm.
- *Color.*—Black.

I claim:

A new and distinct variety of ilex plant substantially as shown and described, characterized by its dwarf, compact, rotundate, and uniform habit of growth slightly taller than its width and with branches dense and elliptical.

No references cited.